United States Patent [19]

Knapp, Jr. et al.

[11] Patent Number: 5,275,802
[45] Date of Patent: Jan. 4, 1994

[54] TUNGSTEN-188/CARRIER-FREE RHENIUM-188 PERRHENIC ACID GENERATOR SYSTEM

[75] Inventors: Furn F. Knapp, Jr., Oak Ridge; Edward C. Lisic, Cookeville; Saed Mirzadeh, Knoxville; Alvin P. Callahan, Harriman, all of Tenn.

[73] Assignee: Martin Marietta Energy Systems, Inc., Oak Ridge, Tenn.

[21] Appl. No.: 898,050

[22] Filed: Jun. 12, 1992

Related U.S. Application Data

[62] Division of Ser. No. 692,110, Apr. 26, 1991, Pat. No. 5,186,913.

[51] Int. Cl.$^5$ .................. A61K 43/00; C07F 13/00
[52] U.S. Cl. .................................. 424/129; 534/10; 424/1.49
[58] Field of Search ............... 424/1.1; 250/432; 423/2, 49, 54, 249; 534/10

[56] References Cited

U.S. PATENT DOCUMENTS

| | | | |
|---|---|---|---|
| 4,280,053 | 7/1981 | Evans et al. | 250/432 PD |
| 4,521,381 | 6/1985 | Douglas et al. | 423/49 |
| 4,572,823 | 2/1986 | Ogata et al. | 423/49 |
| 4,599,223 | 7/1986 | Douglas et al. | 423/49 |
| 4,683,123 | 7/1987 | Knapp et al. | 423/3 |
| 4,859,431 | 8/1989 | Ehrhardt | 423/2 |
| 4,935,222 | 6/1990 | Deutsch et al. | 424/1.1 |
| 5,021,235 | 6/1991 | Pipes | 424/1.1 |

FOREIGN PATENT DOCUMENTS 2005651A 9/1978 United Kingdom .
2009119A 9/1978 United Kingdom .

OTHER PUBLICATIONS

Ehrhardt et al "An Improved Tungsten-188/Rhenium-188 Generator for Radiotherapeutic Applications," Proc. of 34th Ann. Mtg. Society of Nucl. Medicine, Abs. #416 *J. Nucl. Med.* 28, 4, pp. 656-657 (1987).
A. P. Callahan et al "Availability of Rhenium-188 . . . from a Tungsten-188/Re-188 Generator for Therapeutic Applications," IBID, Abs. #417.
R. E. Lewis, "Production of 70-Day Tungsten-188 and Development of a 17 Hour Rhenium-188 Radioisotope Generator," *J. Nucl. Med.* pp. 804-805 (1966).
R. L. Hayes et al, "Rhenium-188 as a Possible Diagnostic Agent," Oak Ridge Associated Universities Medical Division Report, ORAU 101, pp. 74-77 (1966).
Mikheev et al. U.S.S.R. publication, pp. 248-251, 1972.
J. Blachot et al, *International Journal of Applied Radiation and Isotopes*, 20, pp. 467-470 (1969).

*Primary Examiner*—Donald P. Walsh
*Assistant Examiner*—Ngoclan T. Mai
*Attorney, Agent, or Firm*—Joseph A. Marasco; Harold W. Adams

[57] ABSTRACT

A generator system for providing a carrier-free radioisotope in the form of an acid comprises a chromatography column in tandem fluid connection with an ion exchange column, the chromatography column containing a charge of a radioactive parent isotope. The chromatography column, charged with a parent isotope, is eluted with an alkali metal salt solution to generate the radioisotope in the form of an intermediate solution, which is passed through the ion-exchange column to convert the radioisotope to a carrier-free acid form.

2 Claims, 1 Drawing Sheet

TUNGSTEN-188/CARRIER-FREE RHENIUM-188 PERRHENIC ACID GENERATOR SYSTEM

The United States Government has rights in this invention pursuant to contract no. DE-AC05-84OR21400 between the United States Department of Energy and Martin Marietta Energy Systems, Inc., and funded by the Office of Health and Environmental Research.

This application is a division of application Ser. No. 07/692,110, filed Apr. 26, 1991, now U.S. Pat. No. 5,186,913.

FIELD OF THE INVENTION

The present invention relates to methods and systems for generating medically useful radioisotopes, particularly carrier-free radioisotopes in acidic form, and more particularly to methods and systems for generating carrier-free rhenium-188 in the form of perrhenic acid.

BACKGROUND OF THE INVENTION

Rhenium-188 (Re-188) is one of the most attractive radioisotopes for radioimmunotherapy since it can be obtained from a tungsten-188/rhenium-188 generator system. There is currently widespread interest in Re-188 for therapeutic applications. Re-188 has a half-life of 16.9 hours and decays by $\beta^-$ emission with an average energy of 764 keV. Re-188 also emits a gamma photon with an energy of 155 keV in about 15% abundance. The emission of gamma photons is an important aspect of the decay scheme since they can be efficiently detected with the state-of-the-art, widely used, gamma cameras. Determination of the biodistribution with a gamma camera can provide important information on organ distribution. In addition, the biodistribution and kinetic data can be subsequently used for absorbed radiation dose estimates, which is important in determining the effectiveness, safety and efficacy in using Re-188 labeled agents for therapy.

Rhenium is an analogue of technetium (Tc) in chemical behavior, and recent advances in chemistry of Tc, with focus on the biomedical application of Tc-99 m, could in principal be extended to Re-188. As an example of other generator-produced radionuclides used for therapy, yttrium-90 (Y-90) is currently broadly used for antitumor therapy and other medical applications, but does not emit photons which can be imaged, as does Re-188. Tumor therapy with Re-188 labeled antibodies or Re-188 labeled sulfur colloids for treatment of rheumatoid arthritis of the knee joints and other large synovial joints are two major applications of this radioisotope.

Re-188 is obtained in carrier-free state from decay of W-188, ($t_{\frac{1}{2}} = 69.4$ d) in a generator system. The parent isotope, W-188, is produced by W-186 double neutron capture in a nuclear reactor such as is available from the Oak Ridge National Laboratory (ORNL), Oak Ridge, Tenn.

An alumina based W-188/Re-188 generator system was developed at ORNL, and produced Re-188 as a salt. The generator system generally operates as follows. W-188 is loaded onto an alumina column as tungstic acid, and Re-188 is eluted from column with normal saline (0.155N NaCl). The required bolus volume for the quantitative elution of Re-188 depends on the size of the column which in turn is inversely proportional to the specific activity of W-188. In a typical $1 \times 3.5$ cm column filled with 100 to 200 mesh activated alumina loaded with about 30 mg of W (the mass of W containing 100 mCi of W-188 with specific activity of 3.5 mCi/mg) quantitative elution of the Re-188 daughter is achieved with about 20 ml of eluent. Breakthrough of the W-188 parent is generally less than $1 \times 10^{-4}$%.

Another type of W-188/Re-188 generator system recently described is a "Gel Type" system developed at the University of Missouri [G. J. Ehrhardt et al., *Proceedings of the 34th annual meeting*, Society of Nuclear Medicine, 1987, Abstract No. 416], which involves precipitation of low specific activity W-188 with a zirconium salt to form a gel which is then packed in a column and eluted with saline.

Earlier systems include a zirconium oxide column [Lewis et al., *J. Nucl. Med.*, 7, 804–805 (1966) and Hayes, et al., ORAU Medical Division Research Report, ORAU 101 (1966)], and phosphotungstate on alumina [Mikheev et al., U.S.S.R., (1972)]. These methods and systems produce Re-188 in the form of a perrhenate. In another system, tungsten fluoride was absorbed on an anion exchanger and eluted with perchloric acid [Blachot et al., *Int. J. Applied Radiation and Isotopes*, 20, 467–470 (1969)]. That system produced perrhenic acid, but the presence of perchloric acid may render the product impractical for most biological radiolabeling procedures.

Methods for removing the cations in generator column produced Re-188 solutions is important for volume reduction and for radiolabeling procedures. Methods for overcoming the presence of high levels of cations in carrier-free Re-188 solutions is also needed for maximum flexibility for protein labeling and the like. Since Re-188 in the form of perrhenic acid can be used for radiolabeling various ligands, method and apparatus are needed for removing alkali metals from the eluent and provide a concentrated solution of Re-188 perrhenic acid in HCl or $HNO_3$.

OBJECTS OF THE INVENTION

Accordingly, it is an object of the present invention to provide new and improved methods and systems for generating carrier-free Re-188 in the form of perrhenic acid.

It is an object of the present invention to provide a new and radioisotopic medical diagnosis and therapy procedures.

Further and other objects of the present invention will become apparent from the description contained herein.

SUMMARY OF THE INVENTION

In accordance with one aspect of the present invention, the foregoing and other objects are achieved by a generator system for providing a carrier-free radioisotope in the form of an acid which comprises a chromatography column in tandem fluid connection with an ion exchange column, the chromatography column containing a charge of a radioactive parent isotope.

In accordance with another aspect of the present invention, a method for generating carrier-free Re-188 perrhenic acid comprises the steps of:

providing a chromatography column and a cation exchange column;

applying to chromatography column a charge of a W-188;

eluting the chromatography column with a metal salt solution to generate Re-188 in the form of an intermediate solution; and, passing the intermediate solution through the cation exchange column to convert the Re-188 to a carrier-free acid form.

In accordance with another aspect of the present invention, a method for generating carrier-free Re-188 perrhenic acid comprises the steps of:

providing a chromatography column and an anion-exchange column;

applying to the chromatography column a charge of W-188;

eluting the chromatography column with a metal salt solution to generate Re-188 in the form of an intermediate solution containing an ion of the metal;

passing the intermediate solution through the anion-exchange column to retain said Re-188 thereon;

eluting the anion-exchange column with a dilute acid to elute the metal ion; and, eluting the anion-exchange column with a strong acid to elute the carrier-free Re-188 perrhenic acid.

In accordance with a further aspect of the present invention, a method for generating a carrier-free Re-188 in the form of perrhenic acid comprises the steps of:

providing a chromatography column and an cation-exchange column;

applying to the chromatography column a charge of W-188;

eluting the chromatography column with a dilute alkali metal salt solution to generate Re-188 in the form of an intermediate solution of a perrhenate salt; and, passing the intermediate solution through the cation-exchange column to convert the perrhenate salt to carrier-free Re-188 in the form of perrhenic acid.

In accordance with another aspect of the present invention, a method for generating a carrier-free Re-188 in the form of perrhenic acid comprising the steps of:

providing a chromatography column and an anion-exchange column;

applying to the chromatography column a charge of W-188;

eluting the chromatography column with a dilute alkali metal salt solution to generate Re-188 in the form of an intermediate solution of a perrhenate salt;

passing the intermediate solution through the anion-exchange column to retain the Re-188 ion of the perrhenate salt thereon;

eluting the anion-exchange column with a dilute acid to elute, the alkali metal ion; and, eluting the anion-exchange column with a strong acid to elute carrier-free Re-188 in the form of perrhenic acid.

In accordance with another aspect of the present invention, a radioisotopic composition comprises carrier-free Re-188 in the form of perrhenic acid, the perrhenic acid being free of perchloric acid.

In accordance with a further aspect of the present invention, a method for carrying out a medical procedure comprises the steps of:

providing carrier-free Re-188 in the form of perrhenic acid, the perrhenic acid being free of perchloric acid;

reacting the perrhenic acid with a substance to form a medically useful product; and, carrying out said medical procedure using said product.

Figure 1:
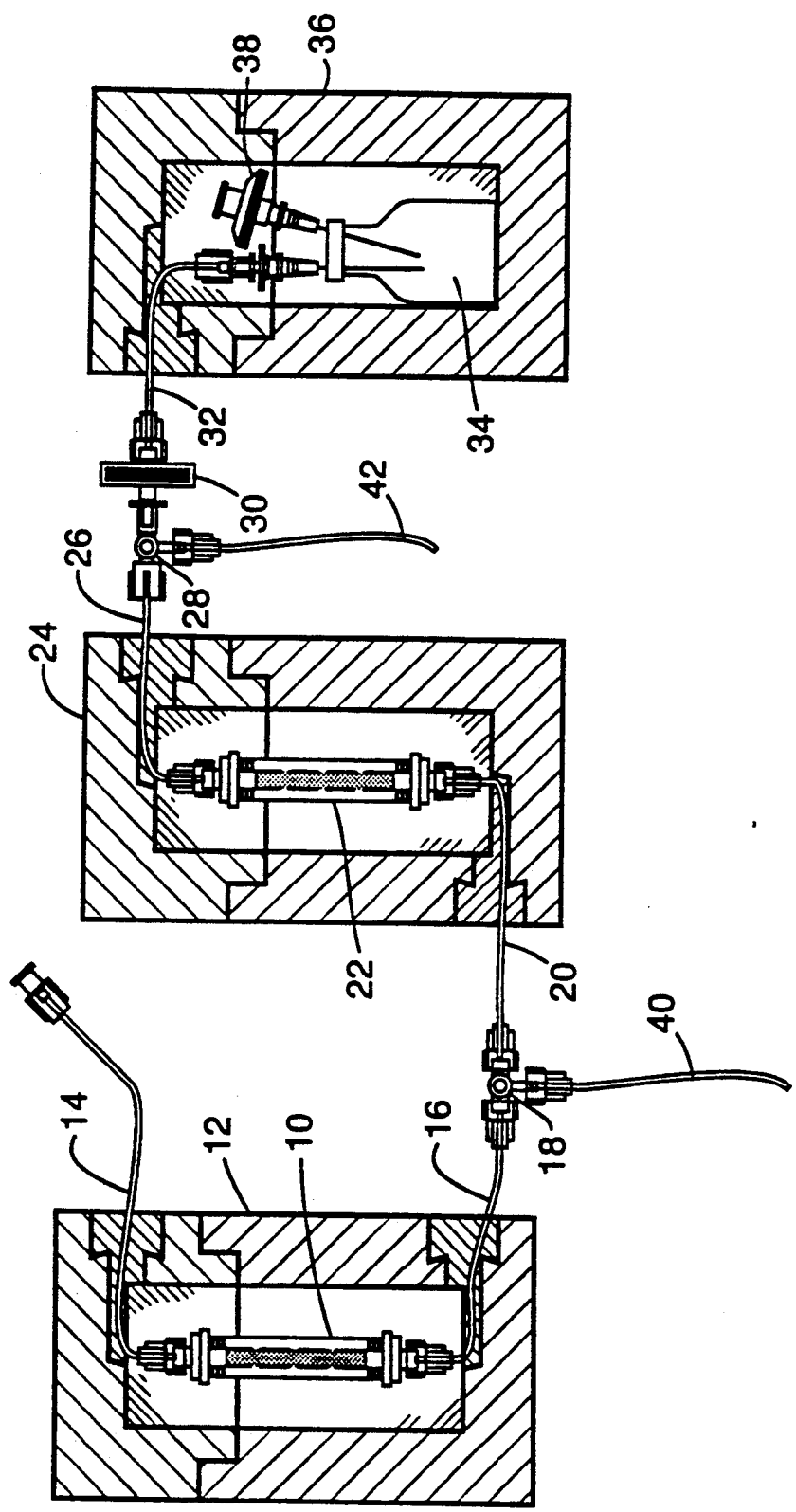
FIG. 1 shows schematically, a perrhenic acid generator system in accordance with the invention.

For a better understanding of the present invention, together with other and further objects, advantages and capabilities thereof, reference is made to the following disclosure and appended claims in connection with the above-described drawing.

DETAILED DESCRIPTION OF THE INVENTION

Method and apparatus involve the use of specific eluents for elution of Re-188 from a generator in fluid tandem with an ion exchange column to provide carrier-free Re-188 perrhenic acid. The generator is a chromatographic column loaded with an inorganic adsorbent such as alumina or silica. Eluent from the generator system, containing the alkali metal (usually sodium) salt of the Re-188 labeled perrhenic acid ($NaReO_4$), is subsequently passed through either an anion or cation exchange column from which the Re-188 labeled perrhenic acid ($HReO_4$) can be obtained.

A convenient method for preparing carrier-free Re-188 in the form of perrhenic acid utilizes an ion exchange column loaded with a cation exchanger. A strong acid cation exchange resin comprised of sulfonic acid functional groups attached to a styrene divinylbenzene copolymer lattice such as or AG ® 50W-X1 resin (tradename used by Bio-Rad Laboratories), or a styrene divinylbenzene copolymer lattice containing paired imidodiacetate ions such as Chelex ®-100 (tradename used by Bio-Rad Laboratories), are suitable. Cation exchange resins do not adsorb Carrier-free Re-188 in neutral solutions. However, alkali metal ions such as $Na^+$ or $K^+$ in the generator eluent are displaced by $H^+$ when eluent is passed through cation exchange column. An important consideration in this method is the capacity of the resin to retain all the alkali metal ions. The chemical form of eluted Re-188 is perrhenic acid since each equivalent of alkali metal ions will liberate one equivalent of $H^+$.

Studies of the alumina W-188/Re-188 generator column have shown that dilute solutions, for example, 0.01M, of several alkali metal salts (LiCl, NaCl, KCl, RbCl, CsCl) elute Re-188 from the alumina very effectively as the respective alkali metal perrhenate salts. The elution profiles of carrier-free Re-188 from the generator were found to be a function of alkali metal concentration in the eluent. Substantially faster elution of Re-188 occurs with higher concentrations of alkali metal ions. Conversely, the lower the alkali metal salt concentrations required for elution of the perrhenate ion, the lower the milliequivalents of alkali metal cation which are retained by the cation exchange column. Thus, the cation exchange can be relatively small.

A generator system to provide carrier-free Re-188 in the form of perrhenic acid is shown in FIG. 1. A W-188/Re-188 generator column 10, which is essentially an alumina chromatography column, is enclosed in a lead shield 12, and has an inlet tube 14. The generator 10 also has an outlet tube 16 which is connected to a first three way valve or stopcock 18, and thence to the inlet tube 20 of an ion exchange column 22, which can be of the cation or anion type. The ion exchange column 22 is enclosed in a lead shield 24, and has an outlet tube 26 connected to a second three way valve or stopcock 28.

The second stopcock 28 is connected through a sterilizing microfilter 30 and an inlet tube 32 to a collection vessel 34, which is enclosed in a lead shield 36, and has a venting filter 38. The stopcocks 18, 28 provide means for rinsing and eluting of the ion exchange column 22 through tubes 40, 42, with the generator column 10 being in fluid isolation. The entire system can be housed in a single lead shield, not illustrated, with valve handles extending through the shielding.

A method for using the above-described generator system is as follows. With the first stopcock 18 open to the cation exchange column 22 and the second stopcock 28 open to the collection vessel 34, the generator column 10 is eluted with 0.01-3.0M, typically 0.155M NaCl solution. This elutes Re-188 from the generator column 10 to the cation exchange column 22 where the Na+ is trapped and H+ is liberated. The Re-188 is eluted into the collection vessel in the form of a concentrated bolus of perrhenic acid. The three-way stopcocks 18, 28 are opened to the cation exchange column 22 and tubes 40, 42 for regenerating the cation exchange column 22.

EXAMPLE I

An alumina W-188/Re-188 generator column was attached in tandem to a cation exchange column with a three-way valve between the union of the two columns. The cation exchange column contained 3.4 g of AG ® 50W-X1 (preequilibrated with 1.0M HCl, followed by copious amounts of $H_2O$). Re-188 was eluted with 1×12 ml of 0.155M NaCl produced Re-188. Results shown in Table 1 indicate that fraction 4-10, a total of 6 ml, contained >95% of the Re-188 activity, the pH value of <1 indicating removal of Na+ ions from the eluent. Therefore, all the Re-188 was eluted as perrhenic acid.

TABLE 1

| Eluted Volume, mL | Counts/Min | % Activity | pH |
|---|---|---|---|
| 1 | 0 | 0 | 5.6 |
| 2 | 7 | 0.04 | 3.2 |
| 3 | 90 | 0.56 | <1 |
| 4 | 993 | 6.27 | <1 |
| 5 | 3102 | 19.60 | <1 |
| 6 | 4657 | 29.42 | <1 |
| 7 | 4248 | 26.84 | <1 |
| 8 | 1707 | 10.78 | <1 |
| 9 | 718 | 4.53 | <1 |
| 10 | 218 | 1.37 | <1 |
| 11 | 86 | 0.54 | <1 |
| 12 | 0 | 0% | <1 |

EXAMPLE II

Carrier-free Re-188 in the form of perrhenic acid was prepared using the apparatus and method described in Example I, with the exception that 0.30M NaCl was used to elute the intermediate sodium perrhenate product. Results are shown in Table 2 and indicate that fraction 3-6, contained >95% of the Re-188 activity in a volume of only 3 ml, the pH value of <1 indicating removal of Na+ ions from the eluent. Therefore, all the Re-188 was eluted as perrhenic acid.

TABLE 2

| Eluted Volume, mL | Counts/Min | % Activity | pH |
|---|---|---|---|
| 1 | 0 | 0 | 5.6 |
| 2 | 264 | 2.26 | 3.1 |
| 3 | 4473 | 38.34 | <1 |
| 4 | 5260 | 45.08 | <1 |
| 5 | 1360 | 11.65 | <1 |
| 6 | 246 | 2.10 | <1 |
| 7 | 64 | 0.54 | <1 |
| 8 | 0 | 0 | <1 |
| 9 | 0 | 0 | <1 |
| 10 | 0 | 0 | <1 |
| 11 | 0 | 0 | <1 |
| 12 | 0 | 0 | <1 |

Another method for preparing carrier-free Re-188 in the form of perrhenic acid utilizes an ion exchange column loaded with a anion exchanger. For Re, the distribution coefficients (defined as $D_v$=amount absorbed per liter resin bed/amount per liter solution) on strongly basic anion exchange resin are $1\times10^3$ and $\sim 1$ in 0.1M and 6M $HNO_3$, respectively. A resin comprised of a quaternary ammonium functional groups attached to a styrene divinylbenzene copolymer lattice such as AG ® 1-X8 (trade name used by Bio-Rad Laboratories) is suitable. On the basis of these large differences in distribution coefficients, carrier-free Re-188 is found to be strongly retained in a small anion exchange column from dilute $HNO_3$ and then eluted with strong $HNO_3$. This discovery provides a basis for separation of Re from eluent cations and other impurities.

EXAMPLE III

An anion exchange column for providing the exchange of perrhenate anion by removal of alkali metal cations was prepared. A W-188/Re-188 generator was eluted with 20 mL of 0.155M NaCl into a beaker containing 0.5 ml of concentrated $HNO_3$ and the solution evaporated to dryness under a heat lamp. The residue was dissolved in 1 mL of 0.16M $HNO_3$ and loaded onto a AG ® 1-X8 Anion Exchange column (100-200 mesh, Cl− form preequilibrated with 0.16M $HNO_3$). By washing with low concentrations of $HNO_3$ (0.16M followed by 1.6M), essentially all of the Re-188 was retained and metal impurities such as $Fe^{+++}$ were removed. Subsequent washing with 6M $HNO_3$ eluted the Re-188 perrhenic acid, as shown in Table 3. The experiment was successfully repeated with $HNO_3$ concentrations of $1.6\times10^{-2}$.

TABLE 3

| Eluent Fractions | | Volume, mL | Re-188 Perrhenic Acid Eluted | |
|---|---|---|---|---|
| | | | Counts/Min | Percent |
| 0.16N $HNO_3$ | (load) | 1 | 0 | 0 |
| 0.16N $HNO_3$ | 1 | 5 | 0 | 0 |
| 1.6N $HNO_3$ | 2 | 1 | 0 | 0 |
| | 3 | 1 | 22 | 0.046 |
| | 4 | 1 | 67 | 0.14 |
| | 5 | 1 | 11,504 | 2.4 |
| 6N $HNO_3$ | 6 | 1 | 410,781 | 85.1 |
| | 7 | 1 | 59,489 | 12.3 |
| | 8 | 1 | 0 | 0 |

A method for preparing carrier-free Re-188 in the form of perrhenic acid using a generator column 10 in tandem fluid connection with an anion exchange column 22 involves a few more steps than the above described method, but has an advantage of impurity removal. The stopcocks 18, 28 are open to tubes 40, 42, and the anion exchange column 22 is preequilibrated with 0.16M $HNO_3$. With the first stopcock 18 open to the anion exchange column 22, the generator column 10 is typically eluted with 0.15M $KNO_3$ or 0.15M $NH_4NO_3$ solution. This elutes the Re-188 from the generator column 10 on to the anion exchange column 22 where it is retained as the perrhenate ion. The three-way stopcocks 18, 28 are opened to the anion exchange column 22 and tubes 40, 42, and the anion exchange column 22 is washed with dilute (0.1M) $HNO_3$, which effectively removes alkali metal cation impurities, but the Re-188 continues to be retained on the anion exchange column 22. Opening the second stopcock 28 to the collection vessel 34, the anion exchange column 22 is eluted with 6N $HNO_3$ which elutes the Re-188 in the form of a concentrated bolus of perrhenic acid.

EXAMPLE IV

An alumina W-188/Re-188 generator column was attached in tandem to an anion exchange column loaded with AG® 1-X8, with a three-way valve between the union of the two columns. Elution of the alumina W-188/Re-188 generator column with 0.155M $NH_4NO_3$ produced Re-188 in the form of ammonium perrhenate, the perrhenate ion being retained on the anion exchange column. No measurable amount of Re-188 eluted from the anion exchange column during this step. The valve was turned to allow elution of the anion exchange column, with the generator column isolated. The anion exchange column was then eluted with 6M $HNO_3$, with fractions analyzed for the presence of Re-188 in the form of perrhenic acid. The results are shown in Table 4.

TABLE 4

| Eluted Volume, mL | Counts/Min |
| --- | --- |
| 1 | 2926 |
| 2 | 4854 |
| 3 | 2046 |
| 4 | 931 |
| 5 | 464 |
| 6 | 276 |
| 7 | 179 |
| 8 | 62 |
| 9 | 17 |

The method is efficient in removing essentially all of the NaCl, and also appears to be most effective in removal of common metal ion impurities such as Fe, Zn, Cu, etc., since these metal ions are not generally adsorbed under the conditions described above.

The complete perrhenic acid generator system with dilute alkali metal eluent and a small (about 1 gm of resin) ion exchange column works reliably for several weeks with daily elutions. Variations in concentration of alkali metal salt eluents and in the size of the ion exchange columns give the subject perrhenic acid generator system a large and effective range of generator shelf life and variability in the concentration and pH of the perrhenic acid product. Although a great variety of cation and anion exchange resins would be effective for carrying out the subject process, the suggested resins are well known, and are available from various purveyors, such as Bio-Rad, Chemical Division, 1414 Harbour Way South, Richmond, Calif.

The perrhenic acid generator system can be built in varying forms. The above-described embodiments involve self-contained ion exchange column regenerating systems that use single exchange columns which can be regenerated via three-way stopcock systems, as illustrated in FIG. 1. A variation utilizes a ion exchange resin column which can be discarded after a single use and replaced with a fresh packaged replacement exchange column. This system has the advantage of not requiring regeneration of the ion exchange column following use, and therefore does not require the associated plumbing. With a supply of replacement columns, the system could be used for several weeks. The system can also be microprocessor controlled using electronic valves. Other variations of this perrhenic acid generator system are possible and further elaboration should be considered as falling within the scope and spirit of the present invention.

Re-188 perrhenic acid produced by the invention is particularly useful for radiolabeling antibodies for tumor therapy, and for the preparation of Re-188 labeled Re-sulfur colloids and other agents for treatment of rheumatoid arthritis of the knee joints and other large synovial joints.

While there has been shown and described what are at present considered the preferred embodiments of the invention, it will be obvious to those skilled in the art that various changes and modifications can be made therein without departing from the scope of the inventions defined by the appended claims.

What is claimed is:

1. A radioisotopic composition comprising carrier-free Re-188 in the form of perrhenic acid, said perrhenic acid being free of perchloric acid.

2. A method for carrying out a medical procedure comprising the steps of:
   providing carrier-free Re-188 in the form of perrhenic acid, said perrhenic acid being free of perchloric acid;
   reacting said perrhenic acid with a substance to form a medically useful product; and,
   carrying out said medical procedure using said product.

* * * * *